United States Patent
Nomura

(10) Patent No.: US 6,677,585 B2
(45) Date of Patent: Jan. 13, 2004

(54) SCANNING CHARGED PARTICLE MICROSCOPE, AND FOCAL DISTANCE ADJUSTING METHOD AND ASTIGMATISM CORRECTION METHOD THEREOF

(75) Inventor: Setsuo Nomura, Nishitama (JP)

(73) Assignee: Hitachi, Ltd., Tokyo (JP)

( * ) Notice: Subject to any disclaimer, the term of this patent is extended or adjusted under 35 U.S.C. 154(b) by 277 days.

(21) Appl. No.: 09/870,512

(22) Filed: Jun. 1, 2001

(65) Prior Publication Data

US 2001/0050338 A1 Dec. 13, 2001

(30) Foreign Application Priority Data

Jun. 12, 2000 (JP) ........................................ 2000-175635

(51) Int. Cl.$^7$ .......................... H01J 37/153; H01J 37/21
(52) U.S. Cl. .................... 250/310; 250/309; 250/396 R
(58) Field of Search ................................ 250/310, 309, 250/396 R

(56) References Cited

U.S. PATENT DOCUMENTS 4,618,766 A * 10/1986 van der Mast et al. .. 250/396 R
4,748,407 A * 5/1988 Brunner et al. ............. 250/310
4,839,520 A * 6/1989 Garth ..................... 250/396 R

FOREIGN PATENT DOCUMENTS

JP 55-46447 4/1980
JP 59-112556 6/1984

* cited by examiner

*Primary Examiner*—Jack Berman
(74) *Attorney, Agent, or Firm*—Dickstein Shapiro Morin & Oshinsky LLP

(57) ABSTRACT

In order to provide a method to easily and surely adjust the focal distance as in a Wobbler apparatus of the transmission type electron microscope method, a crossover 11 of a charged particle beam 2 is established between a charged particle gun 1 and an objective lens 6 and a beam deflection device 4 is provided to deflect the charged particle beam at the crossover point as the supporting point.

A total controller 9 calculates an amount of the out of focus from a moving amount of the microscopic image obtained by deflecting the beam and orders the objective lens power supply to move the microscopic image as the focal distance.

13 Claims, 3 Drawing Sheets

SCANNING CHARGED PARTICLE MICROSCOPE, AND FOCAL DISTANCE ADJUSTING METHOD AND ASTIGMATISM CORRECTION METHOD THEREOF

BACKGROUND OF THE INVENTION

The present invention relates to a scanning charged particle microscope to irradiate a charged particle beam narrowed down onto a sample, and to obtain a microscopic image of the sample on a display unit such as a CRT etc., and especially to a facilitation method of a focusing working and an astigmatism correction working of the microscope.

In a charged particle microscope such as a scanning electron microscope (SEM) and a scanning ion microscope (SIM), a sample face is scanned with the charged particle beam such as the electron beam or the ion beam which is narrowed down, microscopic image is displayed on the CRT by using signals of second particles such as second electrons occured from the sample as brightness modulation signal for the CRT. Focal distance adjusting of the microscopic image is performed usually by regulating a focal distance of an objective lens which met the sample. In the scanning electron microscope of late years, this focal point adjusting working is automatically performed by using a differentiated signal of the second particle signal relating to the the scanning distance thereof. When an operator pushes button, the for focal distance where the differential signal becomes to be the greatest, is obtained, an operating condition of the objective lens changes automatically. The focal point adjusting method that used this differential signal still has an incomplete part. Because the strength of the differential signal is related to contrast (a concentration change of design) of the microscopic image in addition to fineness of the beam, value of the differential signal becomes small and reliability of this automatic focusing method becomes low in the microscopic image being small contrast. Because the contrast in a high magnification image is generally small, this automatic focusing method may not be operated well, when the focal distance in the high magnification image is going to be put together. In addition, this automatic focusing method has a weak point to adjust a focal distance for a sample with a unclear figure.

On the other hand, in transmission type electron microscope (TEM) that principle of the microscopy is basically different from SEM, there is a focal distance adjusting apparatus called Wobbler apparatus, and it has been used as an apparatus being convenient and having high reliability for a long time. In Wobbler apparatus, the electron beam for irradiating the sample is inclined to an optical axis thereof in turn. Operator may observe the microscopic image of the sample magnified on a fluorescence version. If the microscope is out of focus, the image on the fluorescent screen is swung from side to side, and the operator regulates a focal distance of the objective lens so as not to swing the image.

The differential signal in the automatic focusing method of the scanning electron microscope, is extracted as an information of every picture elements of the microscopic image. On the other hand, the swing of the image in Wobbler method of TEM is recognized by extracting and using an information of whole image. The detection of the swing of the image may be executed under extremely high signal to noise ratio and high reliability comparing with the differential signal detection, and the focal distance adjusting is performed without any problem for a low contrast sample. In late years, this principle becomes to be applied in the world of TEM. For example, such apparatus are described in Japanese Patent Leid-open Nos. 59-112556(1984) and 55-46447(1980). The present invention plans to apply such principle in SEM and SIM. If the automatic focusing may be performed by using only two pieces of microscopic image by irradiating the electron beam with different angles to the sample as in the automatic focusing of TEM Wobbler method, such principle is easily used in SEM and SIM. However, if particle beam in conventional SEM/SIM is irradiated to the sample by inclining it as in Wobbler method, only a location difference occurs in proportion to angle of the inclination and any information about the out of focus is not provided in the microscopic image. That is, even if it is in focus, the movement of the microscopic image occurs in the same way and extent of the out of focus is not measured.

SUMMARY OF THE INVENTION

The first object of the present invention is to provide an apparatus which can focus by recognizing an amount of the swing or the move of the microscopic image in the scanning charged particle microscope. The second object of the present invention is to provide an apparatus which can easily correct astigmatism of the scanning charged particle microscope. The third object of the present invention is to provide an apparatus which can focus and can easily correct the astigmatism in a short time, and remarkably reduce damage and contamination of the sample which the beam irradiation causes.

In order to achieve the object mentioned above, in a scanning charged particle microscope of the present invention, an optical system is constituted so as to provide a crossover of the charged particle beam between a charged particle gun and a beam scanning device, and provided a beam deflector so as to deflect the beam at a crossover point as a supporting point.

That is to say, the scanning charged particle microscope in the present invention has a charged particle gun for generating a charged particle beam, an objective lens for irradiating said charged particle beam narrowed down onto a sample, and a scanner for scanning on said sample with said charged particle beam, and the scanning charged particle microscope in the present invention is characterized by comprising a crossover of said charged particle beam being provided between said said charged particle gun and said scanner, and a deflector for deflecting said charged particle beam at said crossover as a supporting point. A beam deflection motion performed by the deflector can be done with a cyclic mode in time repeatedly.

In addition, an image memory to respectively memorize plural pieces of the microscopic images obtained by irradiating the charged particle beams with different deflection-angles, and an operational unit for calculating an amount of figure difference between those microscopic images may be provided in the present invention. Then, it is desirable to have a controller to calculate a focal distance correction amount being necessary for adjusting focal distance of the microscopic image from the amount of the figure difference between plural pieces of the microscopic images, and to set the focal distance of the objective lens to be a value revised by said focal distance correction amount.

In addition, when the charged particle beam is deflected so as to go around a conical surface along a slant line of a circular cone having the crossover as a peak thereof, the correction of the astigmatism can be done based on the information of position moving of the microscopic image by deflecting the beam. That is, an automatic compensation of the astigmatism can be performed by providing an image memory to respectively memorize plural pieces of the microscopic images obtained by using the charged particle beam with different deflection-angle, an operation means for obtaining an ellipse fitting a moving locus of plural pieces of the microscopic images memorized in the image memory, an operation means to calculate a size and a direction of the astigmatism from a length and a leaning angle of major axis and minor axis of an ellipse, and a correction device of the astigmatism driven based on these information.

In the scanning charged particle microscope having the charged particle gun for generating the charged particle beam, the objective lens to irradiate the charged particle beam narrowed down on the sample and the scanner which scans the charged particle beam on the sample in two dimensional, a focal distance adjusting method of the scanning charged particle microscope in the present invention is characterized by providing a crossover of said charged particle beam being provided between said said charged particle gun and said scanner and by regulating the objective lens so as to make a moving amount of the microscopic image minimum when deflecting the charged particle beam at the crossover point as the supporting point.

In the focal distance adjusting method of the scanning charged particle microscope having the charged particle gun for generating the charged particle beam, the objective lens to irradiate the charged particle beam narrowed down on the sample and the scanner which scans the charged particle beam on the sample in two dimentional, the scanner which scans the charged particle beam on the sample in two dimentional and the correction device of the astigmatism, the focal distance adjusting method in the present invention is characterized by providing a crossover of said charged particle beam being provided between said said charged particle gun and said scanner and by regulating the correction device of the astigmatism so as to move the microscopic image to draw a perfect circle when the charged particle beam is deflected so as to go around a conical surface along a slant line of a circular cone having the crossover as a peak thereof.

The scanning charged particle microscope in the present invention can be applied to an elemental analysis of a sample minute part, processing of a minute sample part, and length measurement of the minute sample part. According to the present invention, the focal distance adjusting and the astigmatism correction of the scanning charged particle microscope becomes possible to be easily done, and sample contamination and damage to occur while those working can be reduced.

DETAILED DESCRIPTION OF THE PREFERRED EMBODIMENT

Figure 1:
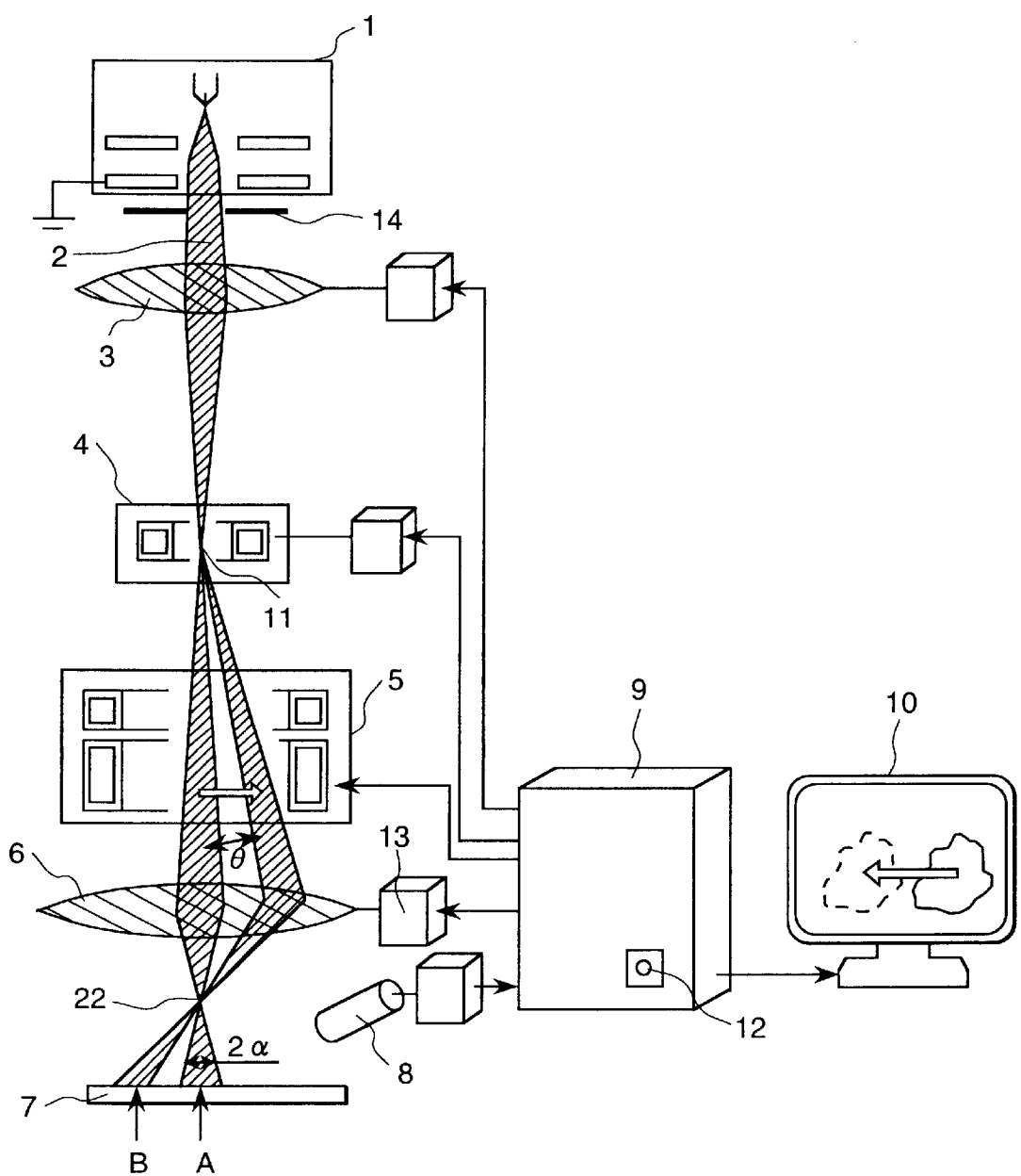
FIG. 1 is a drawing to show an embodiment of the scanning electron microscope applied the present invention.

Referring to drawings, embodiments of the present invention will be explained herein after.
In order to do understanding easily, it will be explained by referring the same number to the element having same function in the following figures. FIG. 1 is a figure for showing an embodiment of the present invention that the present invention is applied to a scanning electron microscope.
An electron beam 2 generated from an electron gun 1 goes through a condenser lens 3, a deflector 4 and a scanner 5, and enters into an objective lens 6. The electron beam 2 is narrowed down by focusing function of the objective lens 6 so as to irradiate a sample 7. In order to get a microscopic image, the electron beam scans two-dimensionally on the sample 7 by the scanner 5, and at the same time, a signal of a second electron generated from the sample 7 is taken in a total controller 9 by a second electron detector 8. The total controller 9 uses this signal as a brightness modulation signal for a CRT 10 and the microscopic image is described on the CRT 10 as a display.

In the above-mentioned embodiment, the constitution characterized in the present invention is;
(1) A deflector 4 is arranged in order to deflect with the electron beam 2, and
(2) (2) a focal distance of the condenser lens 3 is regulated so that the electron beam 2 has a crossover point 11 at a deflection supporting point of the deflector 4. In addition, as the principle to narrow down the electron beam 2 onto the sample 7, a method to get a small spot by projecting the image of the crossover point 11 on the sample 7 with the objective lens 6 is used naturally.

When the electron beam 2 is deflected to a white space on a colored background arrow direction as a beam shown with a dotted line during observing the microscopic image, the following phenomena occurs. As shown in FIG. 1, if the image 22 of the crossover point 11 is not projected with a condition that the focus of the image 22 is fitted on the sample 7, that is, if the image 22 of the crossover point 11 is formed between the objective lens 6 and the sample 7, a central point of the beam scanning on the sample is moved from a point A (a central point before the beam is deflected) to a point B. As a result, the microscopic image displayed on the CRT 10 is changed from a form shown by a continuous line into a form shown by a broken line as shown in the figure. That is to say, the figure moves. When the image of the crossover point 11 is located on the sample 7 precisely, the scanning center location does not change even if the beam is deflected.
This may be easily understood by referring FIG. 1.

By advancing this consideration relating to the lens aberration of the objective lens 6, a moving amount d of the image while the beam is deflected only an angle θ by the deflector 4 is calculated. That is, when the objective lens of a spherical aberration coefficient Cs occurs out focus amount Δf (a difference of the focal distances of the objective lens 6 from a condition that the image of the crossover point 11 is formed on the sample 7), the moving amount d of the image can be shown with an equation (1) as follows.
Here, M1 is a image formation magnification of the objective lens 6 for the electron beam, and M2 is a magnification of the sample image (magnification of the microscope).

$$d = M_2 \cdot (\Delta f + Cs \cdot (\theta/M_1)^2) \cdot (\theta/M_1) \quad (1)$$

Using the equation (1), a control condition of the objective lens which is necessary for adjusting the focal distance of the microscope is obtained. If the focal distance of the objective lens 6 is regulated so that the microscopic image on CRT 10 do not move even if the electron beam is deflected, that is, the moving amount d becomes zero, the out focus amount of the objective lens 6 becomes $-Cs \cdot (\theta/M1)$ 2. By utilizing this principle in the present invention, the focal distance adjusting by recognizing the movement of the microscopic image is performed.

Here, the beam scanning for the microscopic image formation is performed with 1/30 second cycle, and the beam deflection is performed in synchronization with the beam scanning. That is to say, the beam deflection is set and removed every forming one piece of the microscopic image. The microscopic image of odd number piece is displayed on the CRT based on one provided with a condition without the beam deflection, the image of even number piece is displayed on the CRT based on other provided with deflected beam. Based on after image effect of an eye, movement of the image before and after the beam deflection is not recognized as the movement, it looks like a figure of the double image as shown in FIG. 1. When cycle of beam deflection adjusted to be lengthened, it looks like to swing the image instead of the double image.

Operator regulates the focal distance of the objective lens 6 so that the double image figure becomes to be one fold image figure. In the point that the one fold image figure is obtained, a focus button 12 installed in the total controller 9 is pushed down. The image formation magnification of the objective lens 6 for the electron beam, the beam deflection angle θ and the value of spherical aberration coefficient Cs are registered in the total controller 9 previously.

The total controller 9 uses those value, and the out focus amount Δf of objective lens 6 of the time is calculated. Furthermore, the focal distance variation $-Cs \cdot (\theta/M1)2 + 0.25Cs\ \alpha2$ for setting the out focus amount to be in $-0.25Cs\ \alpha2$ is calculated, an objective lens power supply 13 is ordered so that the focal distance is changed according to that value. Here, α is a half-opening angle of the electron beam looked from the sample, and it should be paied attention to be different from the beam deflection angle θ. Here, αis decided based on a diameter of an aperture 14 and the lens magnification of the electron beam optical system, and this is the amount of something already known, too.

Referring to the microscopic image formation principle of the scanning microscope, as the in-focus state of the microscope, the objective lens 6 is controlled so that Δf is not zero and is in a state of out-focus to the amount of $-0.25\ Cs\ \alpha2$. In order to get a sharp microscopic image, a thin scanning beam should be used as possible, and the thinnest beam is provided not in a time when the objective lens 6 focuses the crossover point 11 properly on the sample 7, but in a time when the objective lens 6 focuses insufficiently and so-called a least confusion circle is formed on the sample 7. In this point, the condition of the focal distance adjusting of microscopic image of TEM is completely different from that in SEM. In addition, when strict focus adjusting is not needed the focal distance adjusting working may be completed in a condition which one folded image figure is obtained. In the above embodiment, the focal distance is adjusted for the operator by recognizing folded condition of the microscopic image with CRT. Recognizing a change of the image from the double image to one folded image, is easily performed for the sample image of small contrast, and especially, focal distance adjusting becomes easy for the image of high magnification.

Figure 2:
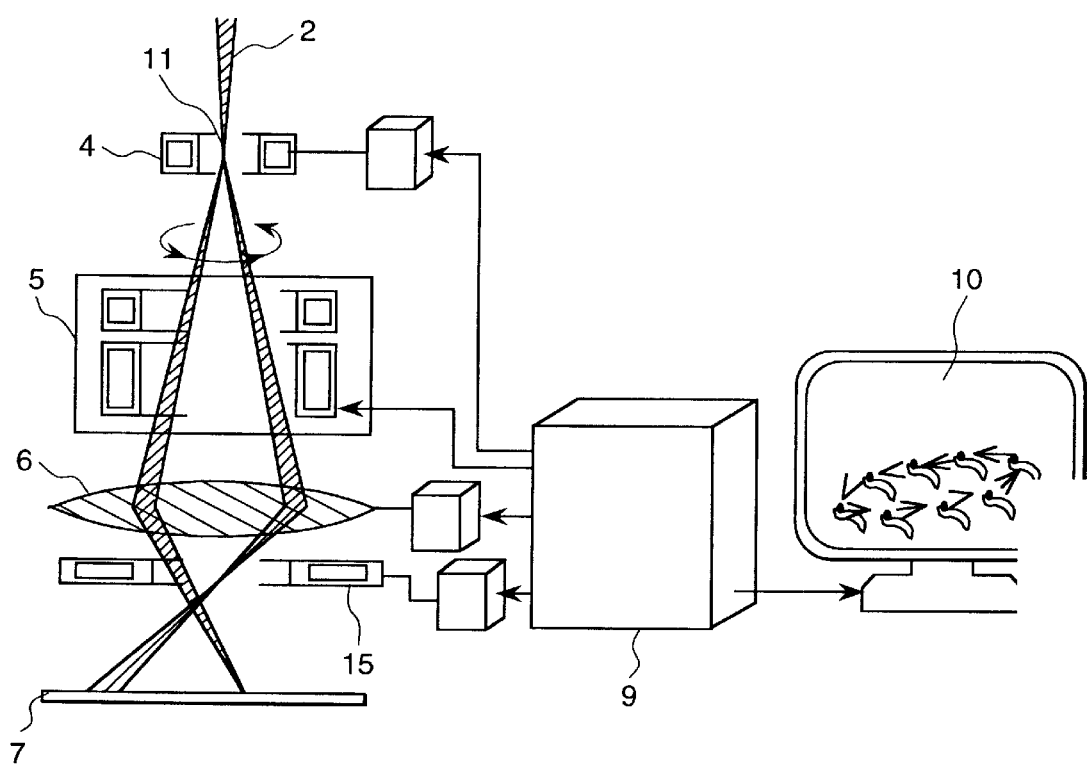
FIG. 2 is a drawing to show an another embodiment of the scanning electron microscope applied the astigmatism correction in the present invention.

FIG. 2 is a drawing to show an another embodiment of the scanning electron microscope applied the astigmatism correction in the present invention.

In FIG. 2, only a sample side looked from the deflector side is drawn. In this embodiment, the electron beam 2 by deflector 4 is deflected like a circle arc arrow shown just under the deflector 4 so as to go around along a conical surface of a cone formed with a peak of the crossover point 11.

An orbiting time of the deflection is (8×1/30) sec, for example, per one circle, and the beam deflection stops 1/30 seconds every 1/8 circle times The electron beam is deflected with scanner 5 two dimensionally on the sample so as to generate the microscopic image. A microscopic image formation time is still 1/30 sec, and in the same way as the above embodiment, it is synchronism with the beam deflection naturally.

The astigmatism in the scanning electron microscopic image occures when the focal distance of the objective lens 6 is not axial symmetry on a lens axis. Then, when the electron beam 2 is circulates as shown in the figure, if there is astigmatism, scanning central point on the sample 7 draws a locus of ellipse instead of complete round. That is, the microscopic image on CRT 10 moves on the ellipse, too. If the electron beam 2 go around when there is not astigmatism, the image on CRT 10 draws a circle having a radius being proportional to the out-focus amount of a predetermined. In this way, the ellipse is drawn at a time with astigmatism and the circle is drawn when there is not the astigmatism. This phenomenon is applied in a correction of the astigmatism of the objective lens 6. That is to say, the operator make the electron beam 2 go around along the conical surface by useing the deflector 4, and observes the microscopic image displayed on the CRT 10 simultaneously. The astigmatism correction device 15 is regulated till the image on the CRT 10 draws complete round to move. The astigmatism correction device 15 has two latches for controlling the direction and amount of the astigmatism, these latches are regulated, and these latch is regulated by the operator till the image on the CRT 10 moves so as to draw the complete round. On the CRT 10 of FIG. 2, when the astigmatism is not revised, it is drawn a figure of the scanning electron microscope to move so as to draw the ellipse.

The correction of the astigmatism was very complicated problem in the conventional scanning electron microscope. When the operator observes the microscopic image set and the extent of the out of focus is not isotropic, for example, the figure seems to flow somehow is obtained, the correction of the astigmatism device was operated to get rid of it. The correction was especially difficult for the sample being in low contrast then. In the present invention, as an information of this anisotropism is distinctly displayed on the CRT as a difference between a circle and an oval, the astigmatism correction working became easy.

Such the astigmatism correction working can be automated. The automation can be performed by letting the beam 2 go around along the conical surface formed with the peak of the crossover point 11 by using the deflector 4 so as to find an ellipse being the most equal to a locus of the moving location of the plurality of the microscopic images (eight pieces of microscopic images in this example explained here) obtained when the beam 2 goes around and to calculate distance of a major axis and a minor axis of the ellipse and a leaning angle thereof. The ellipse the most equal to the locus of moving location of the image, is provided by calculating cross-correlation of eight pieces of the microscopic image, for example. As the lengths of the major axis and the minor axis of the ellipse corresponds to the moving amount d shown with the equation (1), a difference of the focal distance in a direction to cross to a lens axis of the objective lens 6 can be obtained. That is to say, the total controller 9 sends a control order to the power supply of the astigmatism correction device 15 and corrects the astigmatism so as to occur a signal corresponding to control of two latches of the astigmatism correction device described as the above based on the information of the differential of the lengths of the major axis and the minor axis of the ellipse and the turning angle.

Figure 3:
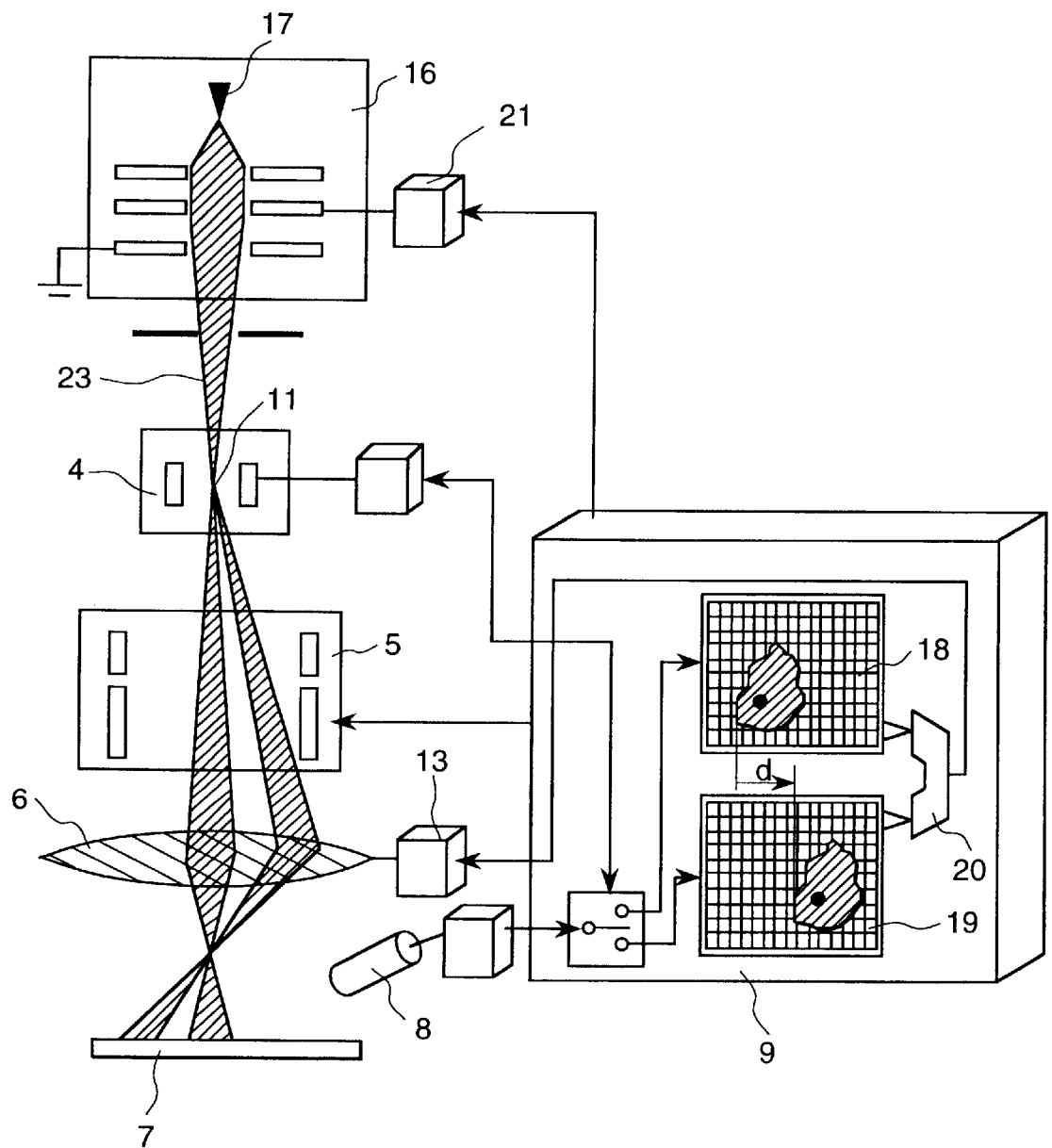
FIG. 3 is a drawing to show an another embodiment of the scanning ion microscope applied the automatic focusing in the present invention.

FIG. 3 is a drawing to show an another embodiment of the scanning ion microscope applied the automatic focusing in the present invention. Because an ion beam is used in the scanning ion microscope, observation of the microscope image causes a damage of the sample. Accordingly, the focal distance adjusting should be completed in a short time of the ion beam exposure as much as possible.

The ion beam 23 generated from an ion gun 16 forms a crossover 11 of the ion beam inside of the deflector 4. The ion gun 16 consists of a liquid metal ion source 17 and three pieces of disk electrodes, and intensity of lens action of the ion gun is constructed to be able to change it arbitrarily by changing a voltage of a center electrode. Therefore, as shown in an embodiment of FIG. 1, the crossover of the ion beam 23 can be prepared into arbitrary location without using the condenser lens especially. That is to say, in an embodiment of FIG. 3, the ion gun 16 is constituted so as to be served as the condenser lens (3), the total controller 9 drives the ion gun lens power supply 21 and orders to form the crossover 11 at a deflection supporting point of the deflector 4. The ion beam generated from the deflector 4 is scanned in two dimentional by the scanner 5, and is narrowed down by the objective lens 6 so as to form the microscopic image.

In the embodiment shown in FIG. 1 as above, the deflection operating of the deflector 4 is performed periodically in time, and the scanning electron microscope image is displayed in CRT every moment. However, in this embodiment, the deflection operating is done only once, the scanning ion microscope images obtained before and after the deflection are respectively saved to be stored in an image memory A18 and an image memory B19. An arithmetic unit 20 calculates cross-correlation of image data of the scanning ion microscope images stored in the image memory A18 and an image memory B19 and the moving amount d of the figure between both imagees is calculated including code of moving direction.

The theoretical formula of the moving amount d is shown in the equation (1) as above already.

A present amount $\Delta f$ of out focus of the objective lens 6 is calculated based on the arithmetic unit 20 calculates the moving amount d of the figures between both images and the above equation (1). Moreover, using a same principle as that in the embodiment shown in FIG. 1, a focal distance correction amount of the objective lens 6 necessary for forming a least confusion circle of the ion beam on the sample 7 is calculated. The total controller 9 orders the objective lens power supply 13 so that the focal distance is changed only this correction amount. That is to say, although the focal distance adjusting of the microscope is executed while observing the several pieces of the microscopic image in an embodiment of FIG. 1 or although the focal distance adjusting is executed by observing the many microscope images moreover in the conventional the scanning ion microscope, the focal distance adjusting can be done by taking in only two pieces of the image in this embodiment. According to the present invention, a focal distance adjusting becomes possible with extremely small amount of the ion beam exposure comparing with that in the conventional method. Therefore, the sample damage occued when the ion beam irradiated is reduced remarkably.

The characteristics to lighten this sample damage can be useful in a method to process a minute part of the sample by using the ion beam (a focusing ion beam machining apparatus) or a method to do an elemental analysis (a minute part second ions mass spectrometer). In any method stated above, as it is necessary to narrow down the ion beam as much as possible, a process to need the focal distance adjusting of the microscopic image is indispensable before each working, the ion beam may disturb the sample in the process, the processing location may not be decided precisely, and there may be a case that the analysis thing disappears. In such a case, when the embodiment shown in FIG. 3 is useful if applied in the electron-beam system because the problems of the sample contamination that the electron beam irradiation causes are reduced remarkably.

The sample contamination makes generating efficiency of second electron lowers, and make quality of the microscope image fall. Image quality deterioration makes length measurement accuracy fall when the scanning electron microscope is utilized in order to measure length of a minute part. In addition, as the contamination means a pile of carbide, a wrong understanding may be given as if original sample includes carbon when elemental analysis of the sample is going to be done using the electron beam. The present invention provide a very useful means to solve these problems.

According to the present invention, the focal distance adjusting and the correction of the astigmatism of the charged particle beam becomes possible easily, a burden of the operator is reduced, and the damage and the contamination of the sample by the beam exposure became to be reduced.

What is claimed is:

1. A scanning charged particle microscope having a charged particle gun for generating a charged particle beam, an objective lens for irradiating said charged particle beam narrowed down onto a sample, and a scanner for scanning on said sample with said charged particle beam, said scanning charged particle microscope comprising:

a crossover of said charged particle beam being provided between said charged particle gun and said scanner; and a deflector for deflecting said charged particle beam at said crossover as a supporting point, wherein said objective lens is adjusted so as to make a moving amount of said microscope image decreased, when said charged particle beam is deflected at said crossover point as the supporting point.

2. A scanning charged particle microscope as defined in claim 1, said scanning charged particle microscope characterized in that said deflector repeatedly deflects said charged particle beam with a cyclic mode of time.

3. A scanning charged particle microscope as defined in claim 1, said scanning charged particle microscope characterized by comprising:

an image memory to respectively memorize plural pieces of the microscopic images obtained by irradiating the charged particle beams with different deflection-angles; and an operational unit for calculating an amount of figure difference between those microscopic images.

4. A scanning charged particle microscope as defined in claim 3, said scanning charged particle microscope characterized by comprising:

a controller to calculate a focal distance correction amount being necessary for adjusting said focal distance of said microscopic image from the amount of the figure difference between plurality of said microscopic images, and to set said focal distance of said objective lens to be a value revised by said focal distance correction amount.

5. A scanning charged particle microscope as defined in claim 1, said scanning charged particle microscope characterized in that said charged particle beam is deflected so as to go around a conical surface along a slant line of a circular cone having said crossover as a peak thereof.

6. A scanning charged particle microscope as defined in claim 3, said scanning charged particle microscope characterized by comprising:

an astigmatism correction device;

an image memory to respectively memorize plural pieces of the microscopic images obtained by irradiating the charged particle beams with different deflection-angles;

an operation means for obtaining an ellipse fitting a moving locus of plurality of said microscopic images memorized in said image memory and to calculate a size and a direction of said astigmatism from a length and a leaning angle of a major axis and a minor axis of said ellipse; and a controller for controlling said astigmatism correction device so as to make said astigmatism controls zero.

7. A focal distance adjusting method of a scanning charged particle microscope having a charged particle gun for generating a charged particle beam, an objective lens for irradiating said charged particle beam narrowed down onto a sample, and a scanner for scanning on said sample with said charged particle beam, said focal distance adjusting method comprising the steps of:

provilding a crossover of said charged particle beam between said charged particle gun and said scanner; and adjusting said objective lens so as to make a moving amount of said microscope image adjusted to be decreased so as to close to the minimum, when said charged particle beam is deflected at said crossover point as the supporting point.

8. An astigmatism correction method of a scanning charged particle microscope having a charged particle gun for generating a charged particle beam, an objective lens for irradiating said charged particle beam narrowed down onto a sample, an astigmatism correction device with a controller for controlling said astigmatism correction device, and a scanner for scanning on said sample with said charged particle beam, said astigmatism correction method comprising the steps of:

providing a crossover of said charged particle beam between said charged particle gun and said scanner; and adjusting said astigmatism correction device so as to move said microscope images on a complete round, when the charged particle beam is deflected so as to go around a conical surface along a slant line of a circular cone having said crossover as said peak thereof.

9. A focal distance adjusting method of a scanning charged particle microscope having a charged particle gun for generating a charged particle beam, an objective lens for irradiating said charged particle beam narrowed down onto a sample, and a scanner for scanning on said sample with said charged particle beam, said focal distance adjusting method comprising the steps of:

providing a crossover of said charged particle beam between said charged particle gun and said scanner; and adjusting said objective lens so as to make a moving amount of said microscope image decreased, when said charged particle beam is deflected at said crossover point as the supporting point.

10. A scanning charged particle microscope having a charged particle gun for generating a charged particle beam, an objective lens for irradiating said charged particle beam narrowed down onto a sample, and a scanner for scanning on said sample with said charged particle beam, said scanning charged particle microscope comprising:

a crossover of said charged particle beam being provided between said charged particle gun and said scanner;

a deflector for deflecting said charged particle beam at said crossover as a supporting point;

an image memory to respectively memorize plural pieces of the microscopic images obtained by irradiating the charged particle beams with different deflection-angles; and an operational unit for calculating an amount of figure difference between those microscopic images.

11. A scanning charged particle microscope as defined in claim 10, said scanning charged particle microscope characterized by comprising:

a controller to calculate a focal distance correction amount being necessary for adjusting said focal distance of said microscopic image from the amount of the figure difference between plurality of said microscopic images, and to set said focal distance of said objective lens to be a value revised by said focal distance correction amount.

12. A scanning charged particle microscope having a charged particle gun for generating a charged particle beam, an objective lens for irradiating said charged particle beam narrowed down onto a sample, and a scanner for scanning on said sample with said charged particle beam, said scanning charged particle microscope comprising:

a crossover of said charged particle beam being provided between said charged particle gun and said scanner;

a deflector for deflecting said charged particle beam at said crossover as a supporting point;

an astigmatism correction device;

an image memory to respectively memorize plural pieces of the microscopic images obtained by irradiating the charged particle beams with different deflection-angles;

an operation means for obtaining an ellipse fitting a moving locus of plurality of said microscopic images memorized in said memory and to calculate a size and a direction of said astigmatism from a length and a leaning angle of a major axis and a minor axis of said ellipse; and a controller for controlling said astigmatism correction device so as to make said astigmatism controls zero.

13. A scanning charged particle microscope having a charged particle gun for generating a charged particle beam, an objective lens for irradiating said charged particle beam narrowed down onto a sample, and a scanner for scanning on said sample with said charged particle beam, said scanning charged particle microscope comprising:

a crossover of said charged particle beam being provided between said charged particle gun and said scanner;

a deflector for deflecting said charged particle beam at said crossover as a supporting point, wherein said charged particle beam is deflected so as to go around a conical surface along a slant line of a circular cone having said crossover as a peak thereof.

* * * * *